(12) United States Patent
Parry et al.

(10) Patent No.: US 11,788,983 B2
(45) Date of Patent: Oct. 17, 2023

(54) SYSTEM HAVING NON-INTRUSIVE FLUID SENSOR

(71) Applicant: Schlumberger Technology Corporation, Sugar Land, TX (US)

(72) Inventors: Andrew J. Parry, Clamart (FR);
Christian Chouzenoux, Clamart (FR);
Eric Grandgirard, Clamart (FR);
Benjamin Charles Perrin, Clamart (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 166 days.

(21) Appl. No.: 17/269,733

(22) PCT Filed: Aug. 21, 2019

(86) PCT No.: PCT/US2019/047385
§ 371 (c)(1),
(2) Date: Feb. 19, 2021

(87) PCT Pub. No.: WO2020/041398
PCT Pub. Date: Feb. 27, 2020

(65) Prior Publication Data
US 2021/0238990 A1    Aug. 5, 2021

(30) Foreign Application Priority Data
Aug. 21, 2018   (EP) .................................... 18306127

(51) Int. Cl.
*G01N 27/22*   (2006.01)
*E21B 47/113*  (2012.01)
*G01N 33/28*   (2006.01)

(52) U.S. Cl.
CPC .......... *G01N 27/226* (2013.01); *E21B 47/113* (2020.05); *G01N 33/2847* (2013.01)

(58) Field of Classification Search
CPC . G01N 27/226; G01N 33/2847; E21B 47/113
See application file for complete search history.

(56) References Cited

U.S. PATENT DOCUMENTS 5,907,099 A   5/1999   Huang et al.
6,345,537 B1  2/2002   Salamitou
(Continued)

FOREIGN PATENT DOCUMENTS

EP   0765465 B1   11/1998
EP   1926991 B1   4/2014
(Continued)

OTHER PUBLICATIONS

Mohamad et al., "Multiphase Flow Reconstruction in Oil pipelines by Portable Capacitance Tomography", Sensors, 2010 IEEE, 2010, pp. 273-278 (Year: 2010).*
(Continued)

*Primary Examiner* — Alexander Satanovsky
*Assistant Examiner* — Asm Fakhruddin
(74) *Attorney, Agent, or Firm* — Jeffrey D. Frantz

(57) ABSTRACT

A technique facilitates nonintrusive monitoring of a fluid constituent within an overall fluid flow. The system and methodology may be used downhole to monitor, e.g., the volume fraction of water in produced well fluid. The system comprises a sensor system combined with a component, e.g. a well component, having a flow passage for receiving a fluid flow. At least a portion of the fluid flow moves through the sensor system which may comprise a main electrode, a guard electrode, and an insulator to isolate the main electrode and the guard electrode. The main electrode and the guard electrode are oriented circumferentially around the (Continued)

fluid flow to obtain capacitance data on the fluid flowing through the sensor system. The capacitance data may be processed to determine the fraction of a specific constituent within the fluid flow, e.g. to determine the volume fraction of water in a well fluid flow.

20 Claims, 12 Drawing Sheets

(56) References Cited

U.S. PATENT DOCUMENTS

| | | | |
|---|---|---|---|
| 6,575,043 | B1 | 6/2003 | Huang et al. |
| 6,755,086 | B2 | 6/2004 | Salamitou et al. |
| 6,758,100 | B2 | 7/2004 | Huang |
| 6,831,470 | B2 | 12/2004 | Xie et al. |
| 6,956,376 | B2 | 10/2005 | Salamitou |
| 7,496,450 | B2 * | 2/2009 | Ortiz Aleman ......... G01F 1/64 702/6 |
| 7,673,525 | B2 | 3/2010 | Huang |
| 7,712,380 | B2 | 5/2010 | Xie |
| 7,717,000 | B2 | 5/2010 | Xie et al. |
| 7,942,065 | B2 | 5/2011 | Xie |
| 7,993,604 | B2 | 8/2011 | Raghuraman et al. |
| 8,027,794 | B2 | 9/2011 | Xie |
| 8,181,535 | B2 | 5/2012 | Huang et al. |
| 8,285,491 | B2 | 10/2012 | Xie et al. |
| 8,360,635 | B2 | 1/2013 | Huang et al. |
| 8,494,788 | B2 | 7/2013 | Atkinson et al. |
| 8,555,729 | B2 | 10/2013 | Xie et al. |
| 8,606,531 | B2 | 12/2013 | Pinguet et al. |
| 8,694,270 | B2 | 4/2014 | Huang et al. |
| 9,010,460 | B2 | 4/2015 | Meeten et al. |
| 9,031,797 | B2 | 5/2015 | Huang et al. |
| 9,395,348 | B2 | 7/2016 | Szabo et al. |
| 9,410,936 | B2 | 8/2016 | Zuo et al. |
| 9,528,869 | B2 | 12/2016 | Xie et al. |
| 9,581,475 | B2 | 2/2017 | Johnson et al. |
| 9,593,575 | B2 | 3/2017 | Xie |
| 9,638,556 | B2 | 5/2017 | Xie et al. |
| 9,645,130 | B2 | 5/2017 | Xie et al. |
| 10,132,847 | B2 | 11/2018 | Xie |
| 10,677,627 | B2 | 6/2020 | Xie et al. |
| 10,724,886 | B2 | 7/2020 | Huang |
| 10,746,582 | B2 | 8/2020 | Huang et al. |
| 10,808,497 | B2 | 10/2020 | Potapenko et al. |
| 10,815,773 | B2 | 10/2020 | Huang |
| 10,890,563 | B2 | 1/2021 | Huang |
| 11,099,168 | B2 | 8/2021 | Xie et al. |
| 11,150,203 | B2 | 10/2021 | Zhu et al. |
| 2005/0204822 | A1 * | 9/2005 | Schumacher ......... G01L 9/125 73/718 |
| 2012/0041681 | A1 * | 2/2012 | Veneruso ......... G01N 33/2823 324/324 |
| 2014/0060204 | A1 * | 3/2014 | Ahmed ............... G01F 1/56 73/861.04 |
| 2017/0285211 | A1 | 10/2017 | Monteiro et al. |
| 2017/0328201 | A1 | 11/2017 | Rodney et al. |
| 2018/0143052 | A1 | 5/2018 | Xie et al. |
| 2020/0003599 | A1 | 1/2020 | Theuveny et al. |
| 2020/0033174 | A1 | 1/2020 | Nogueira et al. |
| 2021/0270647 | A1 | 9/2021 | Xie |
| 2021/0270989 | A1 | 9/2021 | Zhan et al. |
| 2021/0293592 | A1 | 9/2021 | Xie et al. |

FOREIGN PATENT DOCUMENTS

| | | |
|---|---|---|
| EP | 2386834 B1 | 4/2015 |
| EP | 2788726 B1 | 10/2019 |
| EP | 3475684 A4 | 2/2020 |
| EP | 3699395 A1 | 8/2020 |
| WO | WO-2016042317 A1 * | 3/2016 ............. G01F 1/58 |
| WO | 2018022123 A1 | 2/2018 |
| WO | 2001061283 A1 | 8/2020 |
| WO | 2020168064 A1 | 8/2020 |
| WO | 2021011477 A1 | 1/2021 |

OTHER PUBLICATIONS

International Search Report and Written Opinion issued in the PCT Application PCT/US2019/047385, dated Dec. 4, 2019 (12 pages).

* cited by examiner

SYSTEM HAVING NON-INTRUSIVE FLUID SENSOR

CROSS REFERENCE TO RELATED APPLICATIONS

This application claims the benefit of E.P. Application No. EP18306127.4, entitled "SYSTEM HAVING NON-INTRUSIVE FLUID SENSOR," filed Aug. 21, 2018, the disclosure of which is hereby incorporated herein by reference.

BACKGROUND

The production of hydrocarbons, such as oil and gas, involves the drilling of wells into hydrocarbon bearing geologic formations. In general, a wellbore is drilled and a completion system is deployed downhole into the wellbore to facilitate production of the desired wellbore fluids. Depending on the characteristics of a given geologic formation, varying amounts of water may be produced with the hydrocarbon fluid, e.g. oil. Knowledge regarding the amount of water mixed in the overall well fluid being produced can be useful in optimizing production. For example, detection of increasing water content from certain well zones along the completion system may be an indication of potential problems associated with continued production at the same well zone flow rates.

SUMMARY

In general, a system and methodology are provided to facilitate nonintrusive monitoring of a fluid, e.g. monitoring a fluid constituent within an overall fluid flow. For example, the system and methodology may be used downhole to monitor the volume fraction of water and/or other fluid constituent in a produced well fluid. According to an embodiment, a sensor system is combined with a component, e.g. a well component, having a flow passage for receiving a fluid flow. At least a portion of the fluid flow moves through the sensor system which comprises an electrode arrangement for monitoring the fluid flow. For example, the sensor system may comprise a main electrode, a guard electrode, and an insulator to isolate the main electrode and the guard electrode. The main electrode and the guard electrode are oriented circumferentially around the fluid flow so as to obtain capacitance data on the fluid flowing through the sensor system. The capacitance data may be processed to determine the fraction of a specific constituent within the fluid flow, e.g. to determine the volume fraction of water in inflowing well fluid.

However, many modifications are possible without materially departing from the teachings of this disclosure. Accordingly, such modifications are intended to be included within the scope of this disclosure as defined in the claims.

BRIEF DESCRIPTION OF THE DRAWINGS

Certain embodiments of the disclosure will hereafter be described with reference to the accompanying drawings, wherein like reference numerals denote like elements. It should be understood, however, that the accompanying figures illustrate the various implementations described herein and are not meant to limit the scope of various technologies described herein, and.

DETAILED DESCRIPTION

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

With respect to certain embodiments of the present disclosure, a system and methodology are provided to facilitate nonintrusive monitoring of a fluid, e.g. monitoring a fluid constituent within an overall fluid flow. For example, the system and methodology may be used downhole to monitor the volume fraction of water and/or other fluid constituent in a produced well fluid. In a variety of well applications, the well fluid contains a mixture of oil, water and gas. The system and methodology described herein enable continual measurement of the water fraction (or other fluid constituent fraction) as the well fluid travels through a tubing, e.g. a pipe. By way of example, the sensor system may be used to measure capacitance between plates and the capacitance data may be used to infer a dialectic property of the fluid such as a volume fraction of water.

According to an embodiment, a sensor system is combined with a component, e.g. a well component, having a flow passage for receiving a fluid flow. At least a portion of the fluid flow moves through the sensor system which comprises an electrode arrangement for monitoring the fluid flow. By way of example, the sensor system may comprise electrodes disposed in a wall of a pipe to obtain capacitance data as fluid moves through the pipe. The capacitance data may then be used to infer a dielectric property of the fluid such as a volume fraction of water.

In some embodiments, the sensor system may comprise a main electrode, a guard electrode, and an insulator to isolate the main electrode and the guard electrode. The main electrode and the guard electrode are oriented circumferentially around the fluid flow so as to obtain capacitance data on the fluid flowing through the sensor system. The capacitance data may then be processed to determine the fraction of a specific constituent within the fluid flow, e.g. to determine the volume fraction of water in a well fluid flow. For some applications, additional data may be obtained by using segmented, circumferential electrodes to monitor the flowing fluid.

The sensor system may be incorporated into tubing to provide a non-intrusive, e.g. flush-mounted, sensor structure. This type of structure provides a sensor which is more immune to erosion which can otherwise occur due to fluid born particles in, for example, produced well fluid. As a result, the sensor system may be used in many types of downhole well applications and other applications in which particulates may be contained in a flowing fluid. The sensor system configuration also allows the sensor system to operate at higher flow velocities.

Figure 1:
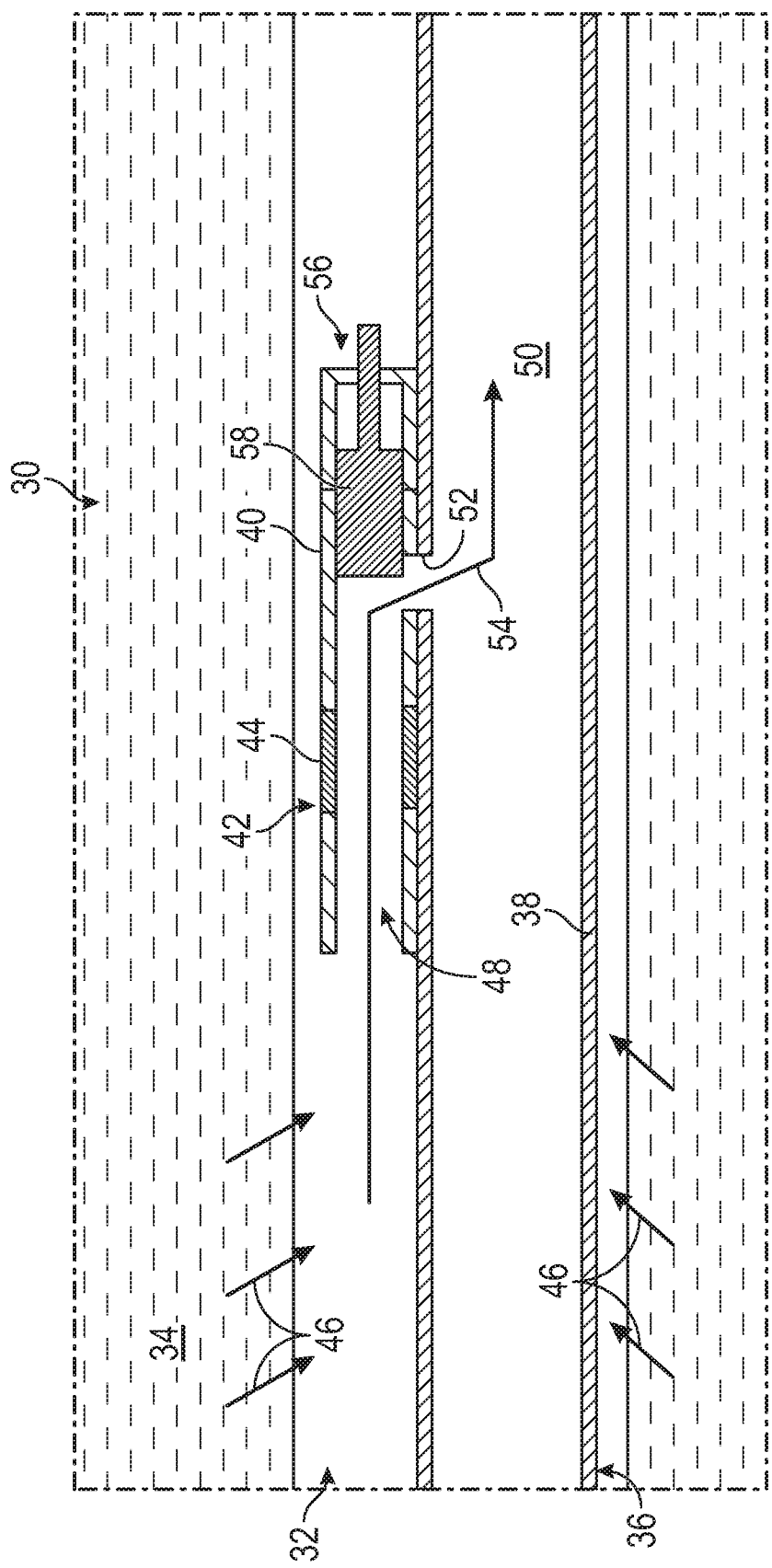
FIG. 1 is a schematic illustration of an example of a well system deployed in a wellbore and having a sensor system for monitoring a fluid characteristic in a fluid flow, e.g. a water fraction in the fluid flow, according to an embodiment of the disclosure.

Referring generally to FIG. 1, an example of a well system 30 is illustrated as deployed in a borehole 32, e.g. a wellbore, drilled into a geologic formation 34. The well system 30 may be in the form of a completion system comprising a well string section 36 having a main tubing 38, e.g. a production tubing, disposed in borehole 32. The main/production tubing 38 may be used for producing a well fluid to the surface. In the illustrated embodiment, the well system 30 also comprises a side pocket tube 40 disposed along the main tubing 38. A sensor system 42 is positioned along the side pocket tube 40 and comprises a sensor 44 arranged circumferentially about the tube 40. It should be noted the sensor 44 may be used along various types of tubes employed in many types of well systems 30 or other types of systems.

As fluid flows from formation 34 (see arrows 46) it enters borehole 32 and then moves into side pocket tube 40. The flowing fluid moves along an interior 48 of side pocket tube 40 and through the interior of sensor 44 before being directed into an interior 50 of main tubing 38 via a passageway 52. The fluid flow through sensor 44 and into interior 50 is illustrated by arrow 54. In some embodiments, a restriction mechanism 56, such as the illustrated choke 58, may be used to control the amount of fluid allowed to flow through passageway 52. For example, the choke 58 may be selectively actuated between a fully closed and a fully open flow position so as to provide control over the amount of fluid flowing from formation 34 and into main tubing 38 at this particular section of the well string 36.

Figure 2:
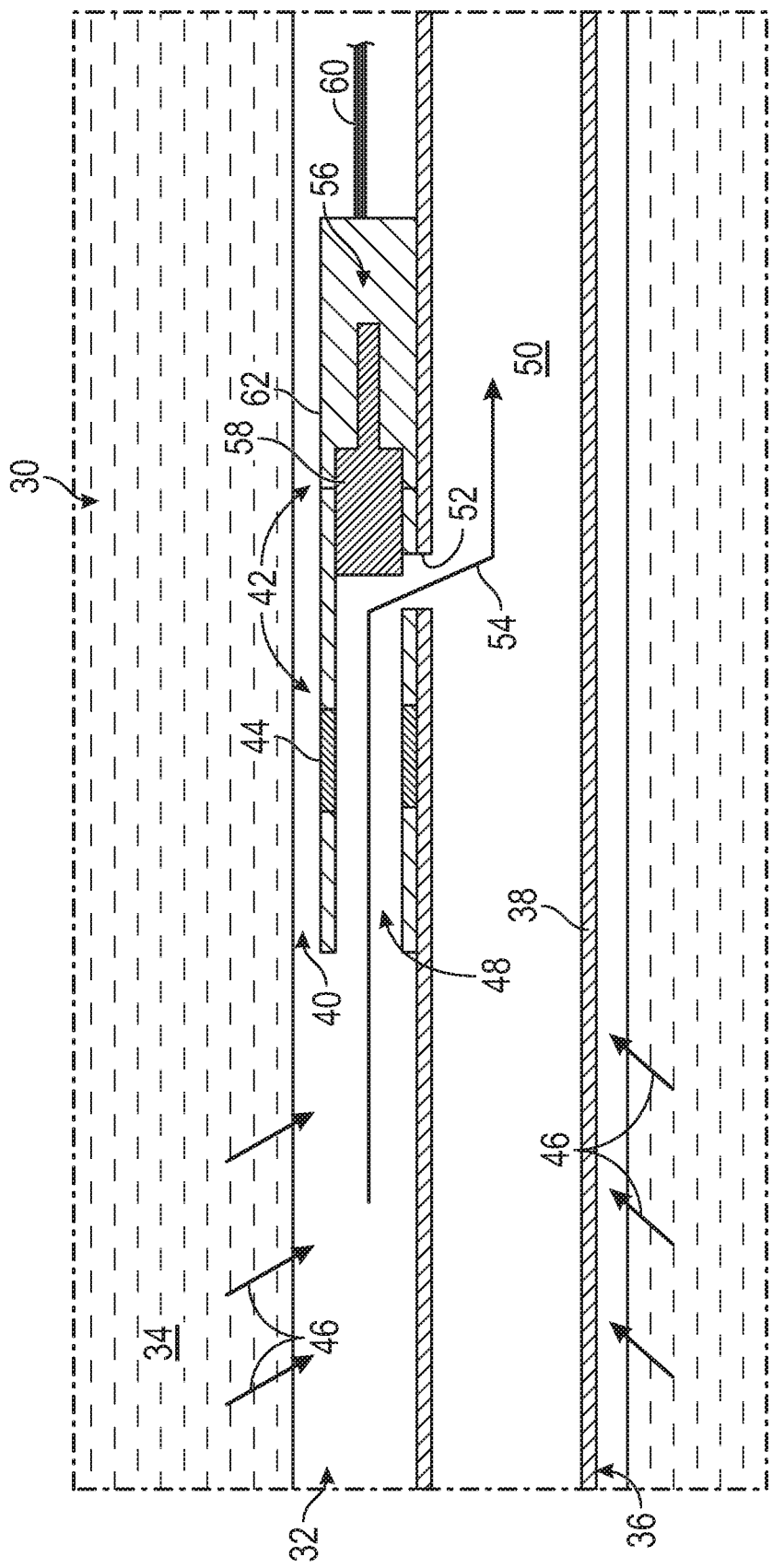
FIG. 2 is a schematic illustration of another example of a well system deployed in a wellbore and having a sensor system for monitoring a fluid characteristic in a fluid flow, according to an embodiment of the disclosure.

With additional reference to FIG. 2, the well system 30 also may comprise a cable 60, such as an electrical cable, routed from the surface down to components of well system 30. In the example illustrated, cable 60 is an electrical cable coupled with an electronics cartridge 62. The electronics cartridge 62 may be part of sensor system 42 and may be operatively coupled with sensor 44 to, for example, receive data from sensor 44. However, the electronics cartridge 62 also may be coupled with restriction mechanism 56 and may be configured to control actuation of restriction mechanism 56 based on inputs from a surface control system or other type of control system.

Accordingly, the electrical cable 60 may be coupled with sensor system 42 and sensor 44 as well as restriction mechanism 56. By way of example, the electrical cable 60 may be used to convey data from sensor 44 to the surface control system or other suitable data processing system. The electrical cable 60 may be used to carry data and/or power signals to and/or from downhole components such as sensor 44 and electronics cartridge 62. It should be noted the cable 60 may comprise other types of cables, such as optical fiber cables, hybrid cables, or other suitable cables for carrying data and/or power.

Figure 3:
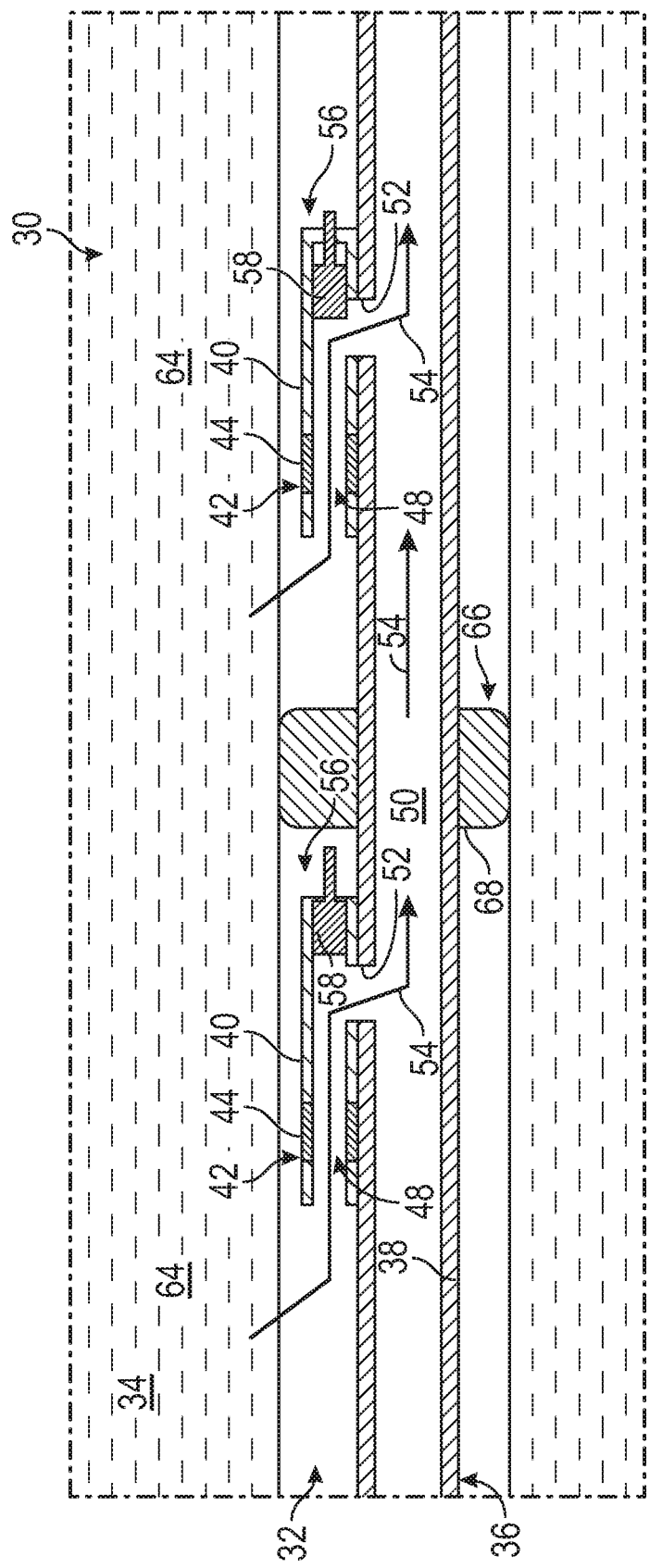
FIG. 3 is a schematic illustration of another example of a well system deployed in a wellbore and having a sensor system for monitoring a fluid characteristic in a fluid flow, according to an embodiment of the disclosure.

Referring generally to FIG. 3, some embodiments of well system 30 may comprise a plurality of sensors 44 positioned at different locations along the well system 30. For example, sensors 44 may be positioned along tubular structures at different well zones 64 disposed along borehole 32. In the illustrated example, a plurality of the side pocket instrumented tubes 40 are positioned along the main tubing 38 to control inflow of well fluid 54 from the different individual well zones 64.

Figure 4:
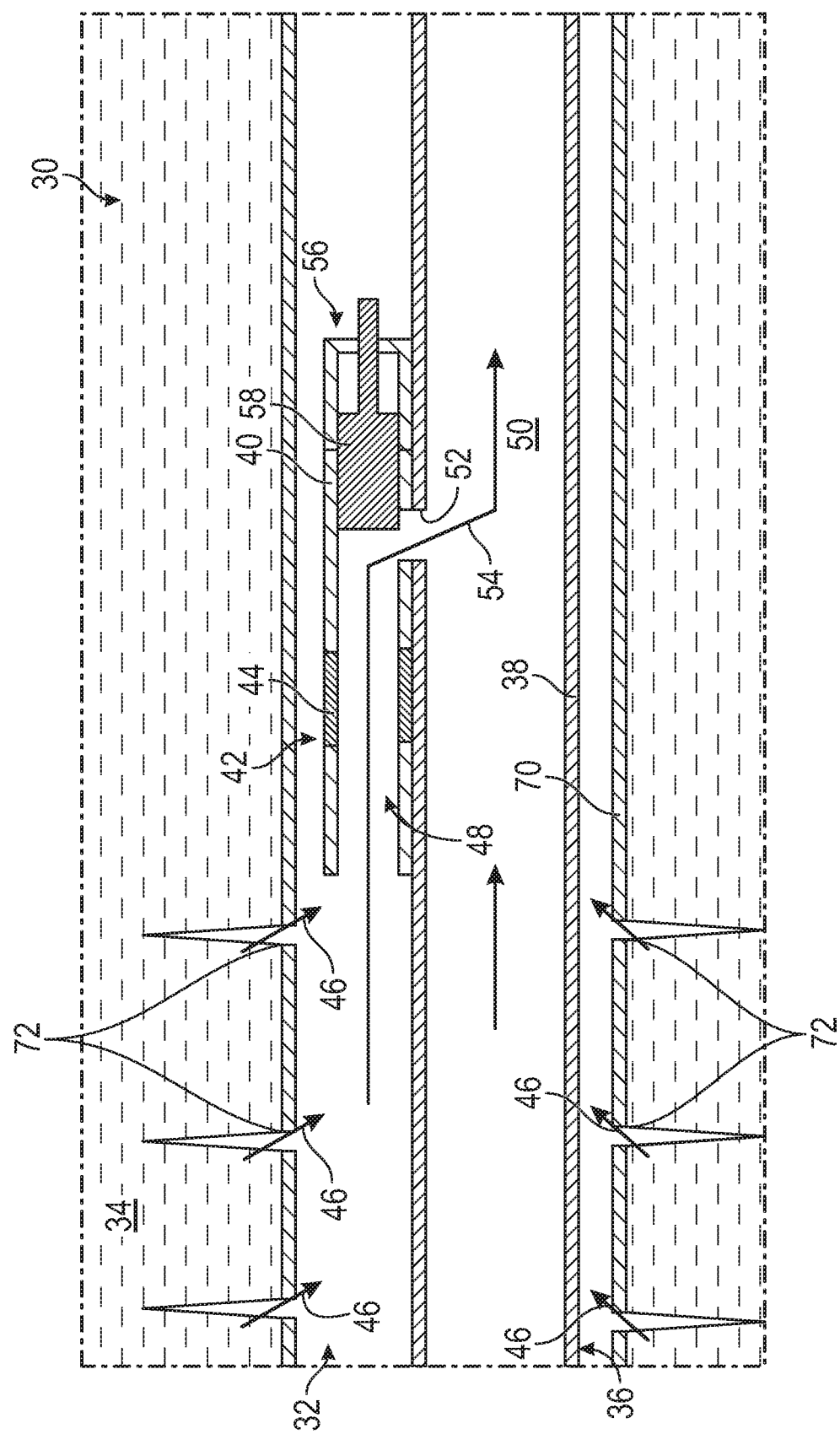
FIG. 4 is a schematic illustration of another example of a well system deployed in a wellbore and having a sensor system for monitoring a fluid characteristic in a fluid flow, according to an embodiment of the disclosure.

The well system 30 also may comprise an isolation device or isolation devices 66 positioned between well zones 64. For example, the illustrated isolation device 66 may comprise a packer 68 disposed about main tubing 38 and expanded into sealing engagement with a surrounding borehole wall of wellbore 32 so as to isolate the two illustrated well zones 64 from each other. In some embodiments, the borehole 32 may be cased with a suitable casing 70, as illustrated in FIG. 4. A plurality of perforations 72 may be formed through the casing 70 and into the surrounding formation 34 to facilitate flow of well fluid 46, 54 from the formation 34 and into interior 50 of main tubing 38.

Figure 5:
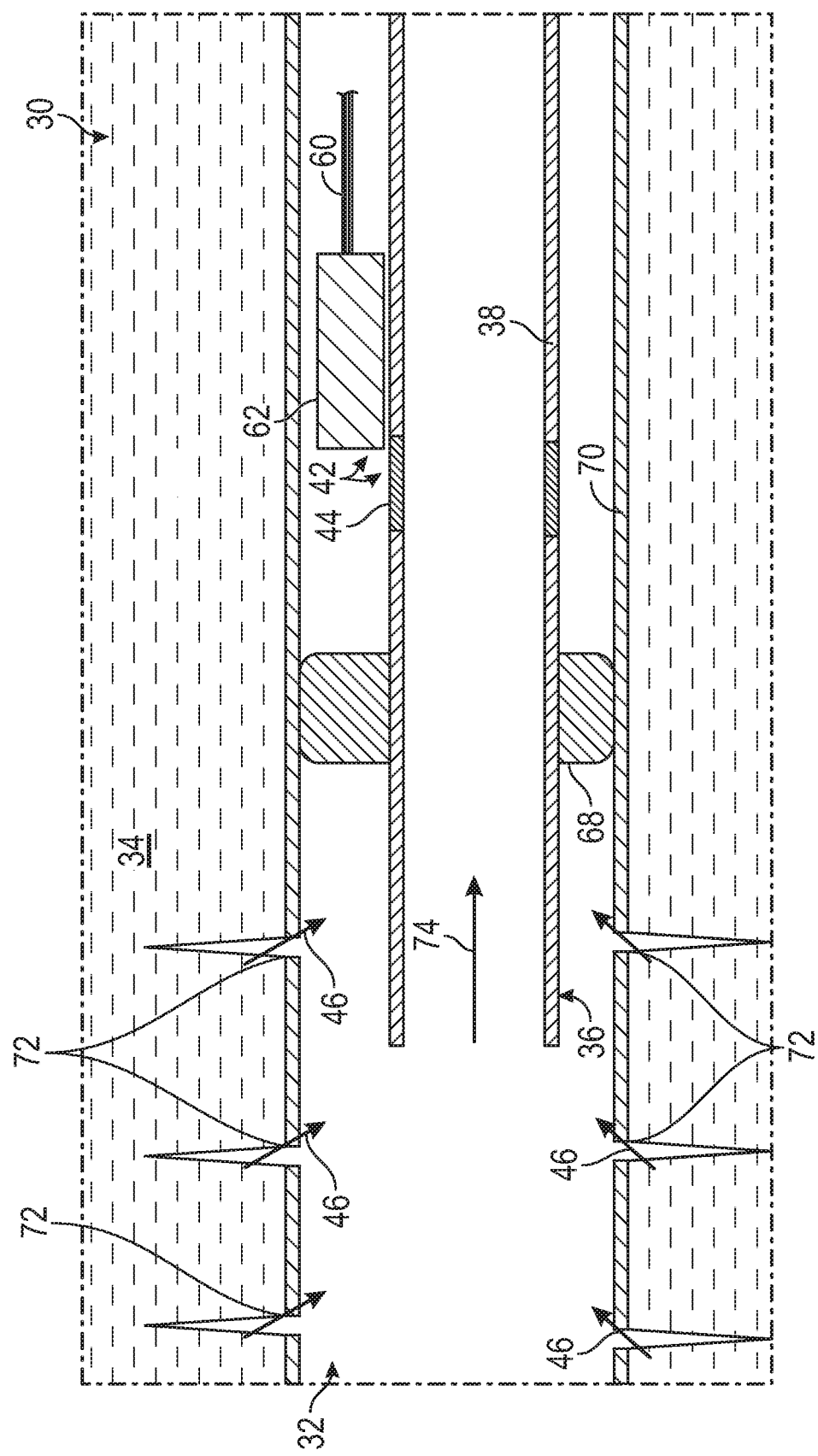
FIG. 5 is a schematic illustration of another example of a well system deployed in a wellbore and having a sensor system for monitoring a fluid characteristic in a fluid flow, according to an embodiment of the disclosure.

Depending on the parameters of a given production operation or other downhole application, the sensor or sensors 44 may be positioned along a variety of tubular structures. As illustrated in FIG. 5, for example, the sensor 44 may be circumferentially positioned along main tubing 38 to monitor a flow of fluid 74 along the tubing interior 50. In this embodiment, the electronics cartridge 62 may be positioned along main tubing 38 and coupled with sensor 44 to obtain and relay sensor data via electrical cable 60. A suitable packer 68, e.g. a production packer or other isolation device, may be positioned between main tubing 38 and, for example, surrounding casing 70 so as to ensure flow of fluid into the interior 50 and through sensor 44.

Figure 6:
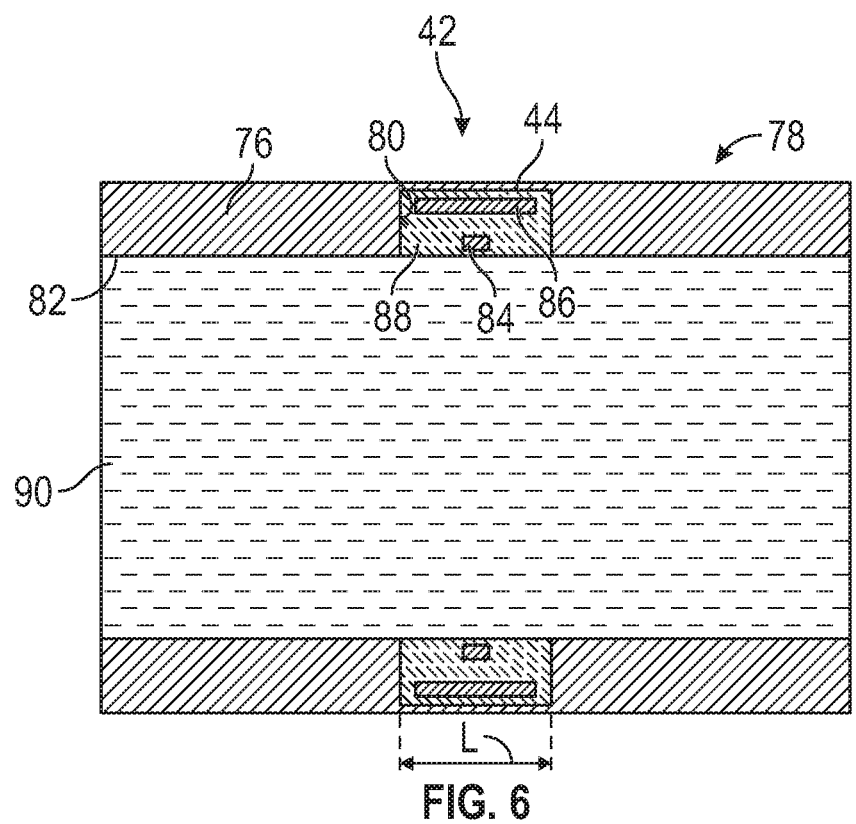
FIG. 6 is a cross-sectional illustration of an example of a sensor system disposed in a tubing, according to an embodiment of the disclosure.

Referring generally to FIG. 6, an embodiment of sensor system 42 is illustrated as comprising sensor 44, having a length (L), disposed in a wall 76 forming a tubing 78. The tubing 78 may be in the form of main tubing 38, side pocket instrumented tube 40, or another type of tubing used in well system 30 or other fluid flow system. In this example, the sensor 44 is disposed in a recess 80 formed in wall 76 and is flush mounted within an interior surface 82 of the tubing 78. Additionally, the sensor 44 may comprise a main electrode 84, a guard electrode 86, and an insulator 88 encapsulating the main electrode 84 and the guard electrode 86. By way of example, the tubing 78 may be conductive and the two electrodes 84, 86 may be enclosed with a ceramic material which may comprise at least part of insulator 88. In some embodiments, the guard electrode 86 may have a greater longitudinal length than the main electrode 84, as illustrated.

Figure 7:
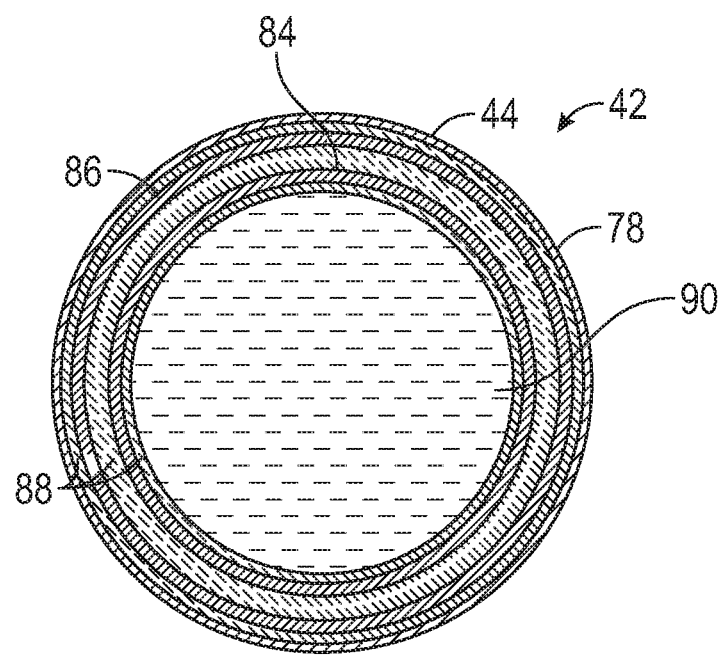
FIG. 7 is a cross-sectional illustration of an example of the sensor system illustrated in FIG. 6 and taken along a plane cutting through a main electrode and a guard electrode used in the sensor system, according to an embodiment of the disclosure.

As further illustrated in FIG. 7, the main electrode 84 and the guard electrode 86 may be circumferential electrodes extending along the circumference of tubing 78. In some embodiments, the main electrode 84 and/or guard electrode 86 may extend a portion of the distance along the circumference of tubing 78. Additionally, at least one of the electrodes, e.g. main electrode 84, may be segmented and have a plurality of segments which extend along portions of the pipe circumference. In the illustrated example, the main electrode 84 and the guard electrode 86 are concentric.

The structure of sensor 44 enables use of sensor 44 in measuring capacitance related to a fluid flowing therethrough. The capacitance data can be processed to determine a constituent fraction in the surrounding fluid, e.g. a water volume fraction. For example, the sensor 44 may be in the form of a water cut probe which measures capacitance of the flowing fluid and relates this to the water volume fraction of the fluid.

The capacitance measured is directly related to the permittivity of the fluid mixture. A mixing law may be employed to infer the water volume fraction from the mixture permittivity. Various mixing laws are available for different types of fluid mixtures. In many types of downhole applications, a mixing law may be selected which is applicable to homogeneous mixtures of water droplets in oil for well mixed cases.

According to an example, a sinusoidal voltage (real) may be applied, via the electronics cartridge 62, on the guard electrode 86 and the main electrode 84 and zero potential on the pipe/tubing 78. The current in the main electrode 84, i, is measured. The capacitance between the main electrode 84 and the pipe/tubing 78 may be determined from the equation:

$$C = \frac{-Im(i)}{2\pi fV}$$

This capacitance can be considered as comprised of two capacitors in series, one for the insulator 88, e.g. ceramic, and one for a fluid 90 flowing along the interior, e.g. interior 48 or 50, as follows:

$$C = \frac{1}{\frac{1}{C_{ceramic}} + \frac{1}{C_{fluid}}}$$

$C_{fluid}$ is proportional to the permittivity of the oil-water mixture. So for a homogeneous mixture:

$$C_{fluid} = K_{geom}\varepsilon_{r,mixture}$$

The permittivity of the mixture is related to the water volume fraction. So we can express water volume fraction given the measured capacitance.

By way of example, the capacitive based water cut sensor 44 may be used when the fluid mixture is oil continuous. This state occurs up to about 30% water volume fraction. Application above this volume fraction also is possible but may introduce additional uncertainties due to variabilities in the transition point between oil and water continuous mixtures.

Figure 8:
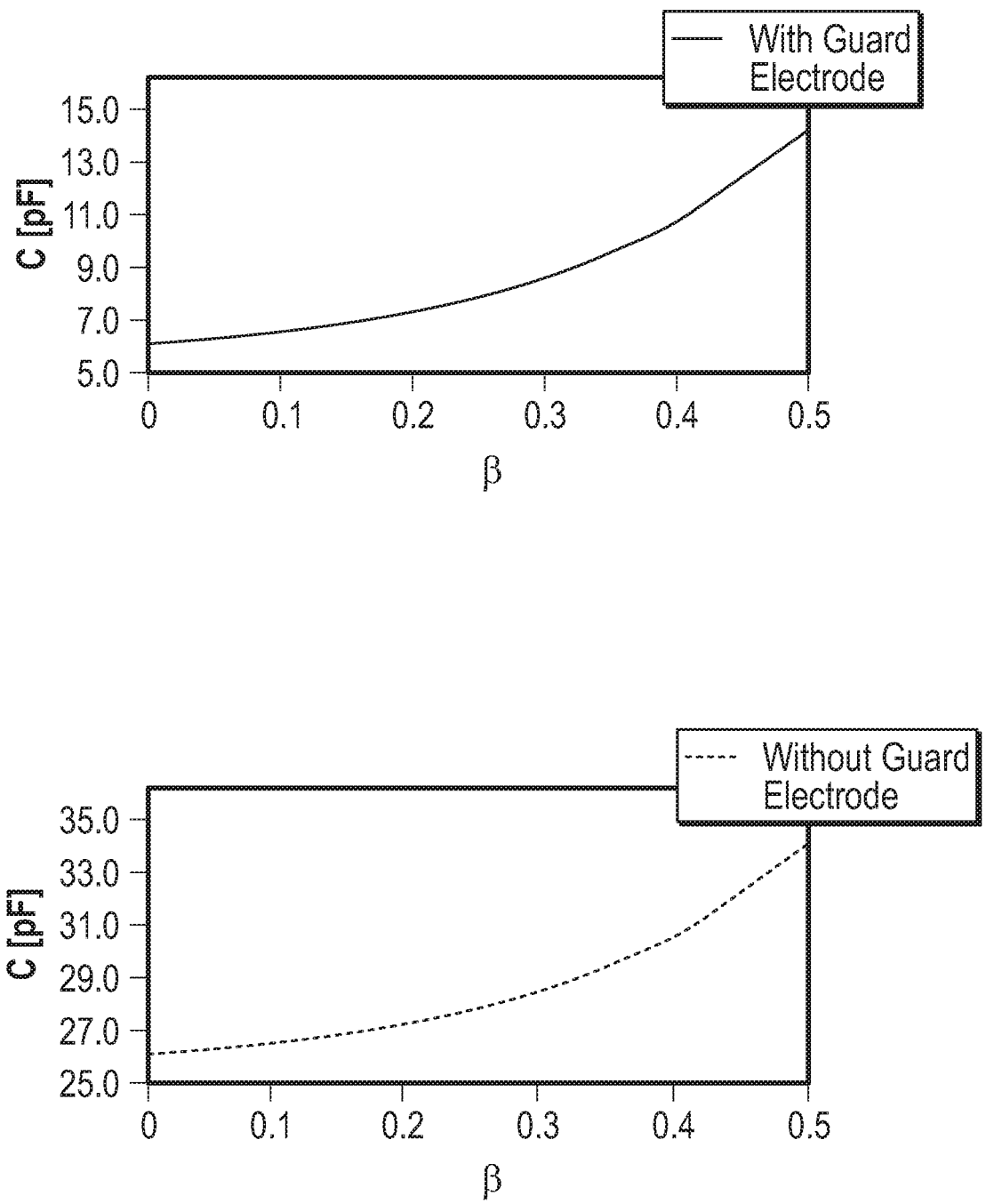
FIG. 8 is a graphical illustration providing graphs of capacitance data measured by the sensor system versus water volume fraction, the data being obtained with a guard electrode and without a guard electrode, according to an embodiment of the disclosure.

Referring generally to FIG. 8, a graphical example is provided to illustrate capacitance between the main electrode 84 and the tubing/pipe 78 as a function of water volume fraction (β) in the oil. In this example, the longitudinal length (L) of the sensor 44 is 10 mm. For comparison, the graphs of FIG. 8 illustrate the capacitance between the main electrode 84 and the tubing/pipe 78 with guard electrode 86 included in the sensor 44 and without the guard electrode 86.

Figure 9:
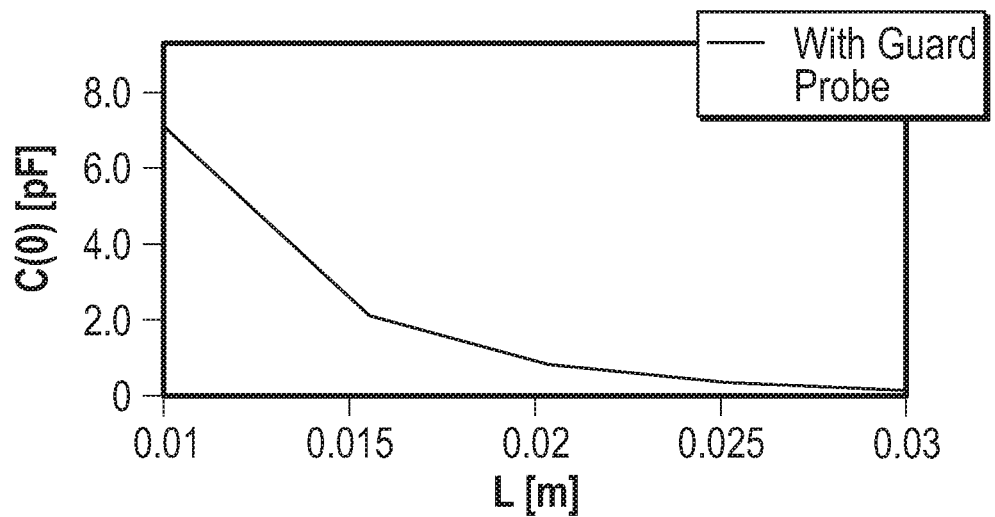
FIG. 9 is a graphical illustration providing graphs of capacitance data measured by the sensor system versus longitudinal length of the sensor system, the data being obtained with a guard electrode and without a guard electrode, according to an embodiment of the disclosure.
Figure 9:
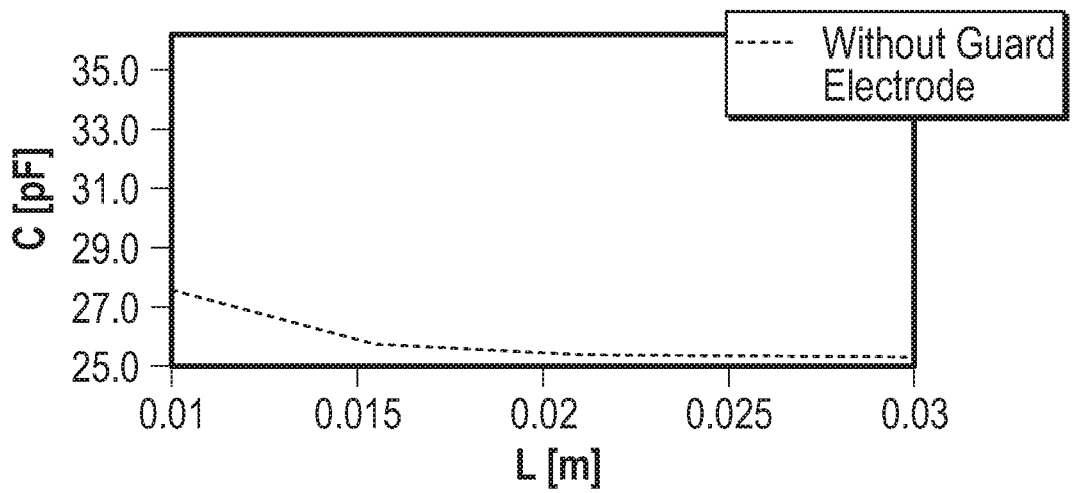

As the length (L) of the sensor 44 changes, the measured capacitance also changes as illustrated graphically in FIG. 9. In this example, the measured capacitance is shown to change substantially in sensors 44 having lengths ranging from 0.01 meters to 0.03 meters. For comparison, the graphs of FIG. 9 illustrate the capacitance between the main electrode 84 and the tubing/pipe 78 with guard electrode 86 included in the sensor 44 and without the guard electrode 86. It should be noted the measured capacitance also changes as the length of the main electrode 84 is increased or decreased relative to the overall length of sensor 44. The overall length of sensor 44 as well as the lengths of sensor components, e.g. main electrode 84, can be optimized for specific applications.

Figure 10A:
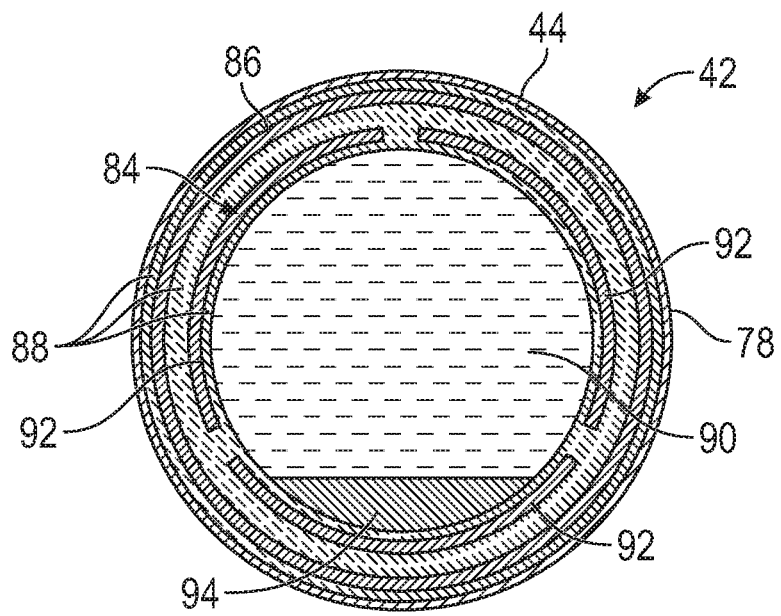
FIGS. 10A and 10B are a cross-sectional illustrations of an example of the sensor system in which the main electrode is separated into a plurality of segmented electrodes, e.g. three segmented electrodes, according to an embodiment of the disclosure.
Figure 10B:
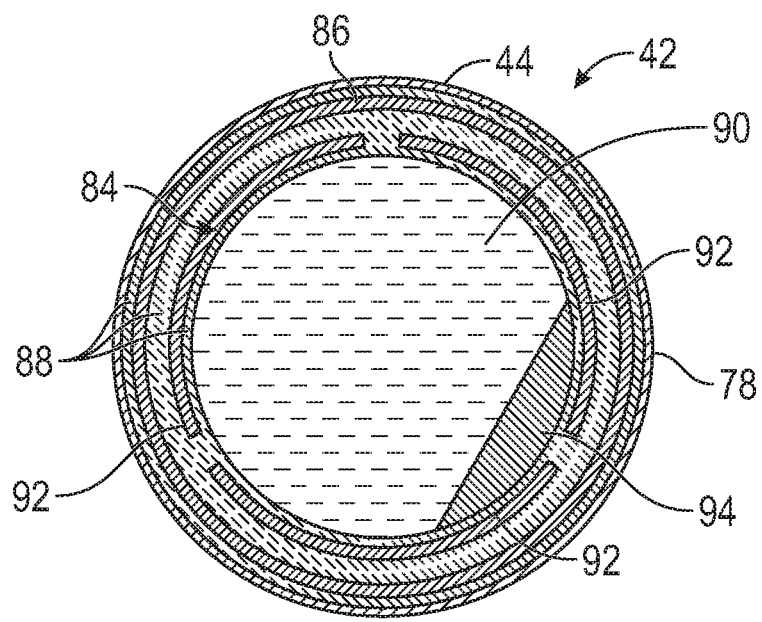

Referring generally to FIGS. 10A and 10B, the sensor 44 also may be constructed in the form of a circumferentially segmented sensor. For example, the main electrode 84 may be divided into a plurality of segments 92 each extending circumferentially along a portion of the circumference of tubing 78. In the example illustrated, the main electrode 84 has been divided into three segments 92 and guard electrode 86 has been formed as one continuous electrode extending along the circumference of tubing 78. The segmenting of main electrode 84 enables monitoring of fluid 90 at different levels within the interior of tubing 78 regardless of the rotational orientation of tubing 78. In other words, the sensor 44 may be constructed so as to be insensitive to installation orientation. Additionally, forming the main electrode 84 with a plurality of segments 92 enables accurate interpretation of water fraction in non-homogeneous mixtures. The sensor 44 may be used to measure volume fraction in, for example, stratified and mixed oil-water flow regimes.

In the example illustrated, the fluid 90 includes a water volume fraction 94 of approximately β=0.1 (10%) disposed at a bottom or 0° orientation along the third electrode segment 92 of the main electrode 84. For the purpose of explanation, various examples are provided with different water fractions 94 located at different circumferential orientations along the electrode segments 92. The other circumferential orientations are provided in degrees from 0° (bottom) in the counterclockwise direction.

In this description, the upper right electrode segment 92 is the first electrode segment and the capacitance between the first electrode segment and the tubing 78 is labeled $C_1$;

the upper left electrode segment 92 is the second electrode segment and the capacitance between the second electrode segment and the tubing 78 is labeled $C_2$; and the bottom electrode segment 92 is the third electrode segment and the capacitance between the third electrode segment and the tubing 78 is labeled $C_3$.

Furthermore the three electrode segments 92 of main electrode 84 are combined with a single guard electrode 86 and the sensor length (L) is 10 mm. In this example, the electrodes are electrically excited with 1 V simultaneously and the capacitances are measured between each electrode segment 92 and the tubing 78 to obtain $C_1$, $C_2$ and $C_3$. For a homogeneous mixture with β=0.1, the capacitance values for $C_1$, $C_2$, $C_3$ are equal to 2.30 pF. For a stratified mixture with β=0.1 and the circumferential orientation of water fraction 94 at 0° (see FIG. 10A), the capacitance values are: $C_1$=2.18 pF; $C_2$=2.19 pF; $C_3$=17.08 pF. If, however, the circumferential orientation of the water fraction 94 relative to electrode segments 92 is at 60° (see FIG. 10B), the capacitance values are: $C_1$=9.12 pF; $C_2$=2.15 pF; $C_3$=9.31 pF.

Additionally, for a homogeneous mixture with β=0.3, the capacitance values for $C_1$, $C_2$, $C_3$ are equal to 2.89 pF. For a stratified mixture with β=0.3 and the circumferential orientation of water fraction 94 at 0°, the capacitance values are: $C_1$=3.79 pF; $C_2$=3.80 pF; $C_3$=19.89 pF. If, however, the circumferential orientation of the water fraction 94 relative to electrode segments 92 is at 60°, the capacitance values are: $C_1$=12.95 pF; $C_2$=2.17 pF; $C_3$=13.14 pF.

The following table provides various examples of capacitance values measured by sensor 44 for various mixed/homogeneous and stratified mixtures at various rotational/circumferential positions within the tubing 78.

| β | State of mixture | $C_1$ [pF] | $C_2$ [pF] | $C_3$ [pF] |
| --- | --- | --- | --- | --- |
| 0.1 | mixed | 2.29 | 2.30 | 2.30 |
| 0.1 | stratified 0 deg | 2.18 | 2.19 | 17.08 |
| 0.1 | stratified 30 deg | 4.59 | 2.17 | 13.89 |
| 0.1 | stratified 60 deg | 9.12 | 2.15 | 9.31 |
| 0.1 | stratified 90 deg | 13.62 | 2.17 | 4.58 |
| 0.3 | mixed | 2.89 | 2.89 | 2.90 |
| 0.3 | stratified 0 deg | 3.79 | 3.80 | 19.89 |
| 0.3 | stratified 30 deg | 8.40 | 2.19 | 17.77 |
| 0.3 | stratified 60 deg | 12.95 | 2.17 | 13.14 |
| 0.3 | stratified 90 deg | 17.51 | 2.19 | 8.40 |

For each orientation and state of mixture, an effective capacitance equal to the capacitance that would exist if the fluid was perfectly mixed can be determined by employing a look-up table for $C_1$, $C_2$, $C_3$ as a function of orientation of stratified layer and water volume fraction or by employing a curve fitted equation. An example of a curve fitted equation is the following second order formula:

$$C_{\text{eff}} = C_h\big[1 + a(C_{max} - C_h) + b(C_{int} - C_h) + c(C_{min} - C_h) + d(C_{max} - C_h)^2 +$$
$$e(C_{int} - C_h)^2 + f(C_{min} - C_h)^2 + g(C_{max} - C_h)(C_{int} - C_h) +$$
$$h(C_{int} - C_h)(C_{min} - C_h) + i(C_{max} - C_h)(C_{min} - C_h)\big]$$

$$C_h = \frac{3}{\frac{1}{c_1} + \frac{1}{c_2} + \frac{1}{c_3}}$$

$$C_{max} = \max\{C_1, C_2, C_3\}$$

$$C_{min} = \min\{C_1, C_2, C_3\}$$

$C_{int}$ = intermediate value of $C_i$, between $C_{min}$ and $C_{max}$

The table below shows the % error due to use of the above formula curve fitted with a large amount of points. As can be seen, the interpretation error in stratified flows is low with less than 8% in the worst case. This error can be improved by employing either look-up tables or higher order fits.

| β | State of mixture | $\frac{C_{\text{eff}} - C_{\text{eff mixed}}}{C_{\text{eff mixed}}} \cdot 100$ |
| --- | --- | --- |
| 0.1 | stratified 0 deg | 1.31 |
| 0.1 | stratified 30 deg | 0.40 |
| 0.1 | stratified 60 deg | 5.47 |
| 0.1 | stratified 90 deg | 0.40 |
| 0.3 | stratified 0 deg | 7.67 |
| 0.3 | stratified 30 deg | 4.90 |
| 0.3 | stratified 60 deg | 3.75 |
| 0.3 | stratified 90 deg | 4.90 |

Figure 11:
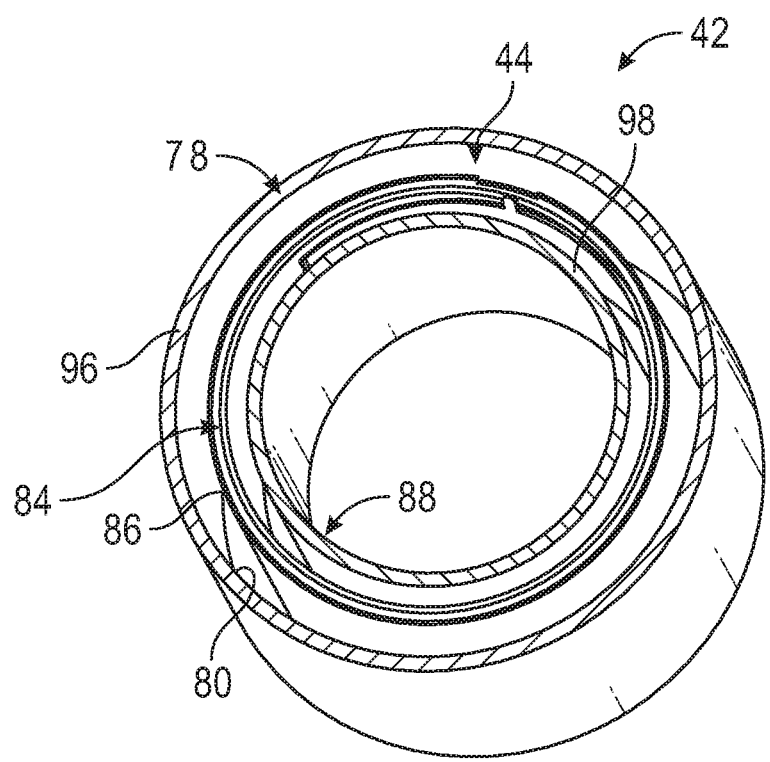
FIG. 11 is an illustration of an example of the sensor system utilizing a main electrode having three annular segmented electrodes combined with a guard electrode between inner and outer sleeves, according to an embodiment of the disclosure.
Figure 12:
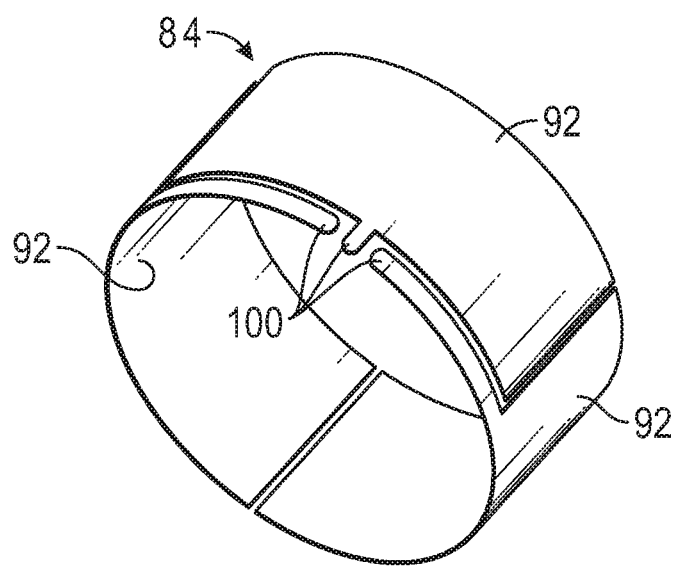
FIG. 12 is an illustration providing an orthogonal view of the main electrode formed of three annular segmented electrodes, according to an embodiment of the disclosure.

Referring generally to FIGS. 11 and 12, another embodiment of sensor 44 in sensor system 42 is illustrated. In this example, the main electrode 84 comprises a plurality of electrode segments 92, e.g. three electrode segments, disposed at a position radially within a single guard electrode 86. The electrodes 84, 86 are positioned within recess 80 of tubing 78 and effectively bounded by an outer metal sleeve 96 (which is the radially outer portion of tubing 78) and an inner insulating sleeve 98, e.g. a ceramic sleeve. The ceramic insulating sleeve 98 may be used to provide resistance to erosion and corrosion as fluid 90 flows therethrough. The insulating sleeve 98 may be part of the overall insulator 88 encapsulating the main electrode 84 and guard electrode 86. In this example, each of the electrode segments 92 comprises a connector tab 100 (see FIG. 12) which may be routed to a common location for electrical connection with electronics cartridge 62.

Figure 13:
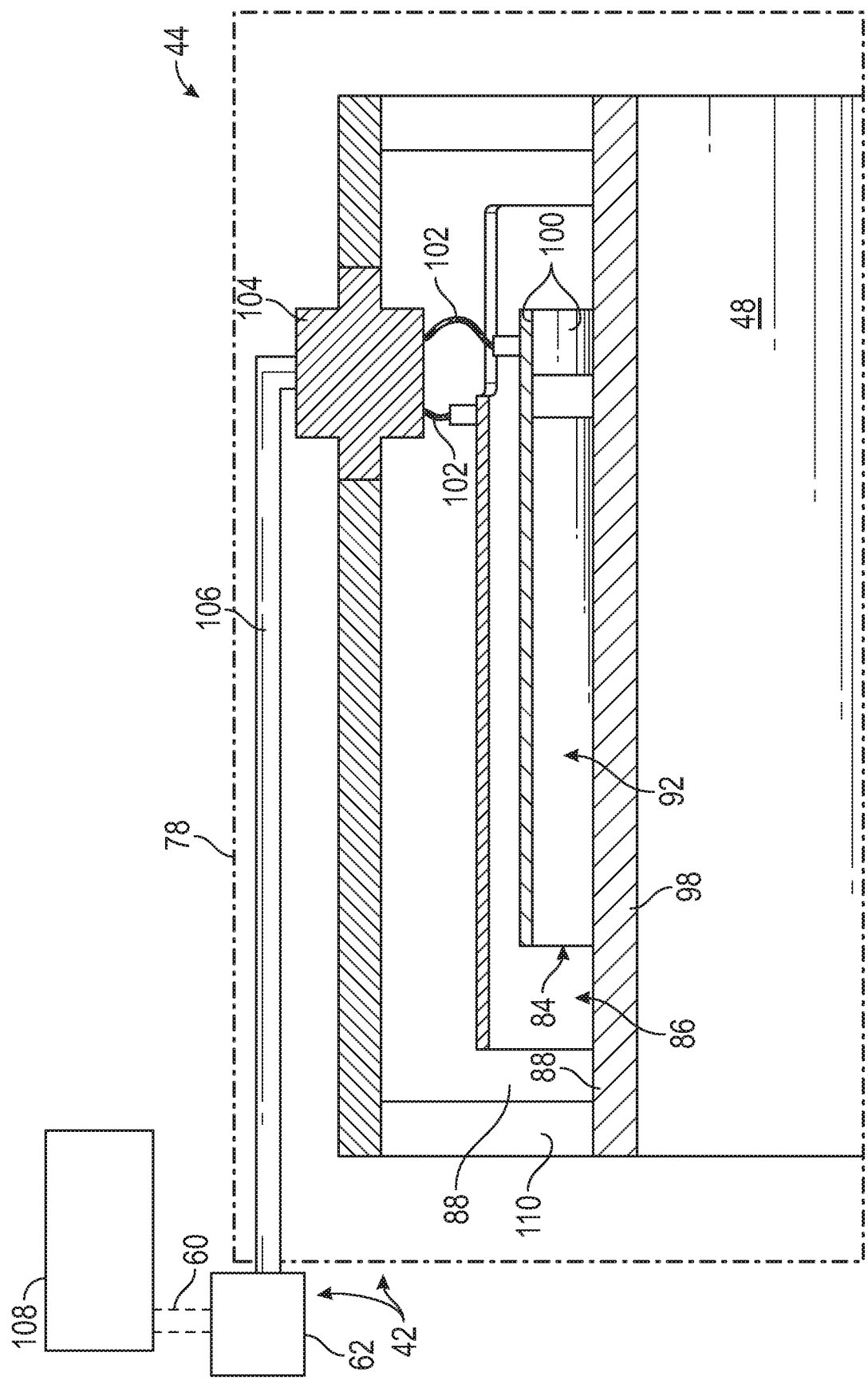
FIG. 13 is a schematic cross-sectional illustration of an example of the sensor system coupled with a control line for carrying data and/or power, according to an embodiment of the disclosure.
Figure 14:
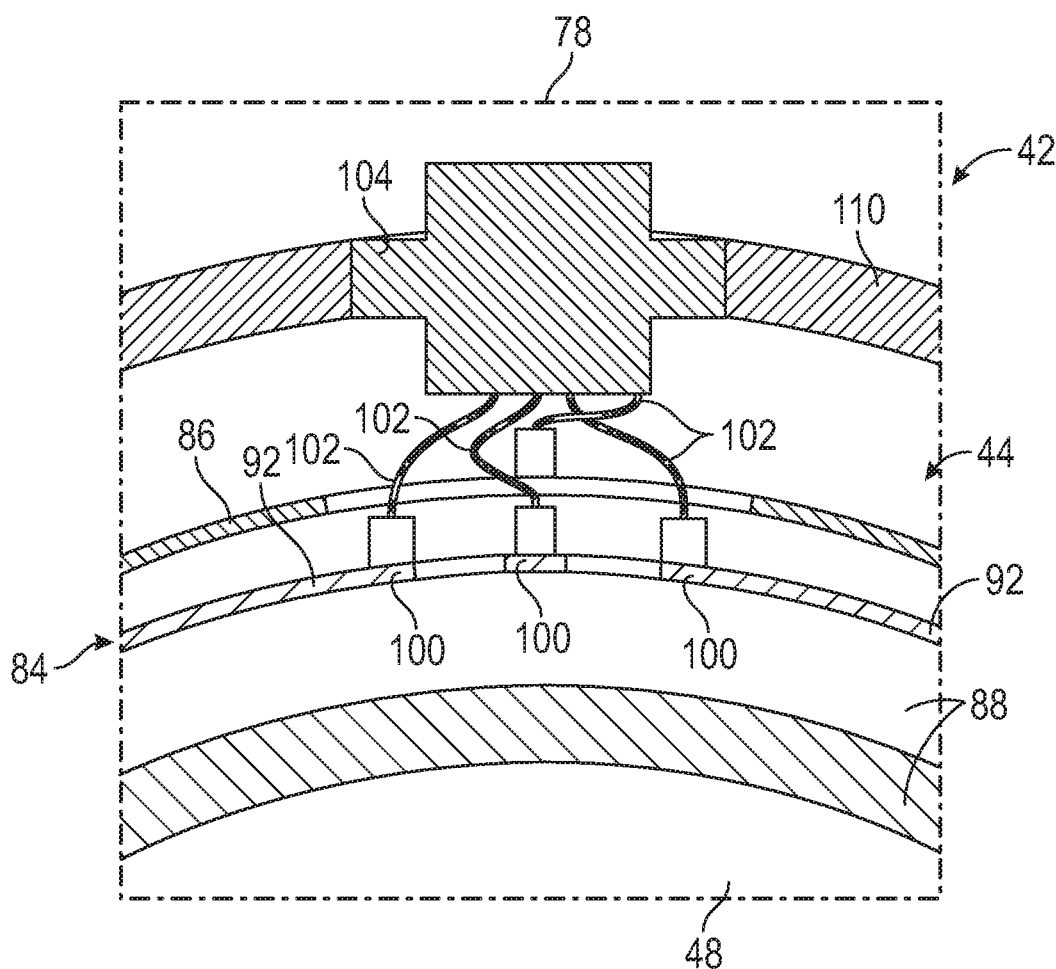
FIG. 14 is another schematic cross-sectional illustration of an example of the sensor system coupled with the control line for carrying data and/or power, according to an embodiment of the disclosure.

As illustrated in FIGS. 13 and 14, for example, the connector tabs 100 of electrode segments 92 as well as guard electrode 86 may be connected to electrical conductors 102, e.g. wires, which are routed through a bulkhead 104. The electrical conductors 102 may be electrically coupled with electronics cartridge 62 via a control line 106, e.g. a shielded, jacketed twisted triples cable, coupled with bulkhead 104. The electronics cartridge 62 may, in turn, be coupled with a suitable processing system 108 via communication line 60. Processing system 108 may be located at the surface or at another suitable location. By way of example, the processing system 108 may be a computer-based control system. Capacitance data obtained via sensor 44 is processed via the processing system 108, as described above for example, to determine a constituent fraction, e.g. a water fraction, in the fluid 90 flowing through tubing 78.

The sensor system 42 and sensor 44 may have various configurations for use in a variety of applications. With additional reference to FIG. 13, an embodiment of sensor system 42 may comprise main electrode 84 and guard electrode 86 disposed in recess 80 which is lined with a protective body 110, e.g. a body formed of Inconel® or other suitable material. The bulkhead 104 is disposed through protective body 110. Additionally, the protective body 110 is filled with an insulation material, e.g. an epoxy, and bounded on the radially inward side via insulating sleeve 98, e.g. a ceramic (zirconia) insulating sleeve, to form part of the insulator 88 encapsulating electrodes 84, 86.

In embodiments described herein, the guard electrode 86 is used to focus the current emanating from the main electrode 84, e.g. main electrode segments 92, into the fluid 90. The guard electrode 86 removes the effective capacitance between the main electrode 84 and the exterior of tubing 78. As the longitudinal sensor length (L) is increased and the longitudinal length of the main electrode is maintained at, for example, 2 mm, the capacitance level decreases; the relative change in capacitance as a function of water volume fraction $\beta$ increases; and the absolute change in capacitance as a function of $\beta$ decreases. For a given length L, e.g. 30 mm, and as the longitudinal length of the main electrode 84 is increased from, for example, 2 mm to 22 mm, the capacitance level increases; the relative change in capacitance as a function of $\beta$ decreases; and the absolute change in capacitance as a function of $\beta$ increases. It should be noted the lengths provided are given as examples to facilitate explanation of the operation of sensor system 42 and should not be construed as limiting. The sensor 44 and electrodes 84, 86 may have various lengths and sizes depending on the parameters of a given application. Additionally, the electrodes 84, 86 may be made of copper or other suitable, conductive materials.

Dividing the main electrode 84 into three segments 92 and then measuring the individual capacitances between each segment 92 and the tubing 78 enables interpretation of the distribution of relative permeability in the pipe cross-section. The three segments 92 may each cover 120° of the circumference of tubing 78 or another suitable portion of the circumference for a given application. As described above, for the case of fully stratified fluid flows it is possible to determine an effective capacitance equal to the capacitance that would occur if the fluid mixture was homogeneous. With the aid of a second order polynomial, this effective capacitance can be determined to within about 8.0%. Higher order formulae or look-up tables can provide even better interpretation.

The sensor system 42 may be used in many types of well applications. For example, sensors 44 may be used along instrumented tubes disposed in sequential well zones. However, individual or plural sensors 44 may be used along various tubular members, including production tubing, to monitor characteristics, e.g. water fraction, of fluid flowing therethrough. Additionally, various types of processing/control systems may be used to process capacitance data obtained from the sensor or sensors 44.

Although a few embodiments of the disclosure have been described in detail above, those of ordinary skill in the art will readily appreciate that many modifications are possible without materially departing from the teachings of this disclosure. Accordingly, such modifications are intended to be included within the scope of this disclosure as defined in the claims.

What is claimed is:

1. A system for use in a well, comprising:
    a completion system deployed in a wellbore and including a first internal flow path through which a well fluid is produced;
    a sensor system comprising:
        a pipe including a second internal flow path through which at least a portion of the well fluid flows;
        a sensor including a main electrode, a guard electrode, and an insulator encapsulating the main electrode and the guard electrode, wherein the main electrode, the guard electrode, and the insulator are disposed in a wall of the pipe and are circumferentially arranged around the second internal flow path of the pipe, and wherein an inner surface of the insulator is flush with the second internal flow path; and
    a processing system coupled to the sensor system and configured to determine a fraction of water in the well fluid from capacitance data obtained from the sensor.

2. The system as recited in claim 1, wherein the main electrode and the guard electrode extend continuously around the entire circumference of the second internal flow path pipe.

3. The system as recited in claim 1, wherein the main electrode is segmented around the circumference of the second internal flow path of the pipe.

4. The system as recited in claim 1, wherein the sensor is disposed in a circumferential recess formed in the wall of the pipe around the second internal flow path.

5. The system as recited in claim 1, wherein the main electrode comprises copper.

6. The system as recited in claim 1, wherein the guard electrode comprises copper.

7. The system as recited in claim 1, wherein the insulator comprises a ceramic material.

8. The system as recited in claim 1, wherein the main electrode and the guard electrode are formed as concentric rings.

9. The system as recited in claim 8, wherein the guard electrode has a greater longitudinal length than the main electrode.

10. The system as recited in claim 3, wherein the main electrode comprises three segments extending circumferentially within the wall of the pipe.

11. A system, comprising:
    a well component having a flow passage for receiving a fluid flow; and
    a capacitance sensor system through which at least a portion of the fluid flow is directed, the sensor system comprising a main electrode and a guard electrode oriented circumferentially around the fluid flow, wherein the main electrode and the guard electrode are isolated from one another by an insulator.

12. The system as recited in claim 11, wherein the main electrode, the guard electrode, and the insulator are disposed in a wall of the well component such that the insulator is flush with an inner surface of the flow passage.

13. The system as recited in claim 12, wherein the main electrode extends continuously around the entire circumference of the flow passage.

14. The system as recited in claim 12, wherein the main electrode is segmented around the circumference of the flow passage.

15. The system as recited in claim 11, wherein the well component is coupled into a downhole well system.

16. The system as recited in claim 15, further comprising a processing system coupled to the capacitance sensor system, wherein the processing system is configured to determine a fraction of water in the fluid from capacitance data obtained from the sensor system.

17. A method, comprising:
    deploying a pipe downhole into a borehole, the pipe including a flow path and a capacitance sensor embedded in a wall of the pipe, the sensor including a main electrode, a guard electrode, and an insulator;
    flowing a downhole fluid through the sensor;
    using the main electrode and the guard electrode to obtain capacitance data as the downhole fluid flows through the sensor; and
    processing the capacitance data to determine a water fraction in the downhole fluid.

18. The method as recited in claim 17, wherein deploying comprises deploying the sensor downhole with a well fluid production completion.

19. The method as recited in claim 17, wherein the main electrode and the guard electrode are rings that extend around an entire circumference of an inner surface of the pipe.

20. The method as recited in claim 17, wherein the main electrode is segmented and includes a plurality of segments that extend around an inner surface of the pipe.

* * * * *